United States Patent [19]
Bauman

[11] 3,942,195
[45] Mar. 9, 1976

[54] HAIRPIECE ANCHOR

[75] Inventor: Jack Bauman, Santa Monica, Calif.

[73] Assignee: Dura-Hair International, Inc., Beverly Hills, Calif.

[22] Filed: Feb. 18, 1975

[21] Appl. No.: 550,178

[52] U.S. Cl. ............................... 3/1; 128/330
[51] Int. Cl.² ........................................ A61F 1/00
[58] Field of Search .......................... 3/1; 128/333

[56] References Cited
UNITED STATES PATENTS

| | | | |
|---|---|---|---|
| 3,694,819 | 10/1972 | Meyer | 3/1 |
| 3,858,247 | 1/1975 | Bauman | 3/1 |
| 3,862,453 | 1/1975 | Widdifield | 3/1 |

Primary Examiner—Channing L. Pace

[57] ABSTRACT

Removably located within an elongated epithelium-lined tract, or tunnel, surgically formed in the subcutaneous layer of the wearer's scalp is the elongated subdermal portion of a scalp anchor. The anchor includes an external portion attachable to a hairpiece. A plurality of such anchors securely yet removably retains the hairpiece in the desired position on the scalp.

A web at the junction of the subdermal and external portions enhances the wearer's comfort by reducing the unit pressure on the adjacent end of the tract in the event that force is exerted against the anchor by the hairpiece; and for hygienic reasons the web is constructed so as to provide channels for the circulation of air in the subdermal tract.

4 Claims, 5 Drawing Figures

HAIRPIECE ANCHOR

BACKGROUND OF THE INVENTION

Surgically installed scalp anchors for hairpieces are disclosed in my U.S. Pat. No. 3,553,737; and various types of scalp anchors installed in surgically formed subdermal tracts in the scalp are shown and described in my U.S. Pat. No. 3,858,247.

The foregoing embodiments serve their purpose in a very satisfactory manner but do not preclude the development of new generation devices capable of providing additional beneficial results.

SUMMARY OF THE INVENTION

The invention relates to new and useful improvements in devices for removably securing a hairpiece to the scalp.

It is an object of the invention to provide a removable scalp anchor which reliably and hygienically, yet comfortably, secures a hairpiece to the wearer's scalp.

It is another object of the invention to provide a removable hairpiece anchor which is capable of resisting a substantial force tending to dislodge the hairpiece and of accomplishing this without causing undue discomfort to the wearer.

It is a further object of the invention to provide a hairpiece anchor which can readily be installed and removed, yet which when installed, securely positions the hairpiece against both angular displacement on the scalp and separation of the hairpiece from the scalp.

It is an additional object of the invention to provide a generally improved hairpiece anchor.

DETAILED DESCRIPTION OF PREFERRED EMBODIMENT

While the hairpiece anchor of the invention can assume various configurations the hereinafter shown and described embodiment is a preferred one.

Figure 1:
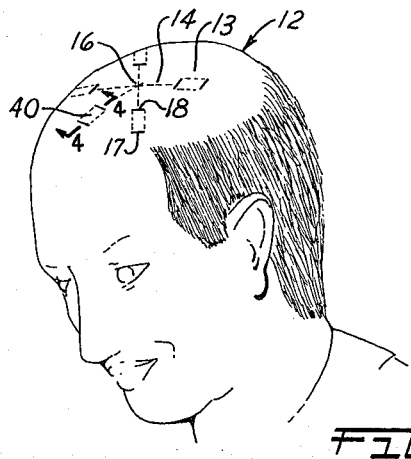
FIG. 1 is a perspective view of a scalp in which a plurality of subdermal tracts has been surgically formed.

At a suitable time prior to the installation of the hairpiece itself, the wearer's scalp 12 will have had surgically formed therein a plurality of subdermal tracts 13, arranged in a suitable pattern, such as the generally pentagonal arrangement illustrated in FIG. 1.

Each of the tracts 13 includes a longitudinal axis 14 preferably converging at a central location 16 on the scalp.

Figure 4:
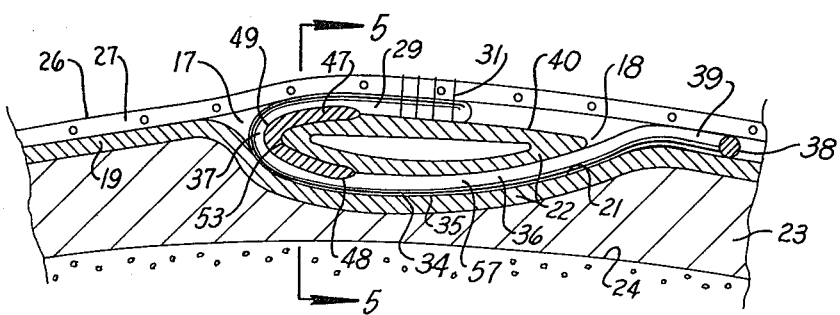
FIG. 4 is a fragmentary sectional view, to a greatly enlarged scale, of a tract lined with epithelium, the plane of the section being indicated by the line 4—4 in FIG. 1, and showing in median longitudinal section a hairpiece anchor installed therein; and, FIG. 5 is a fragmentary transverse sectional view, to a greatly enlarged scale, emphasizing the air circulation channel provided by the lower anchor web and the snug confinement of the underlying skin surface by the web structure, the plane of the section being indicated by the line 5—5 in FIG. 4.

As appears most clearly in FIGS. 1 and 4, each tract includes a spaced pair of linear openings 17 and 18 in the epidermis 19, or outer skin layer, subdermally connected by a tunnel 21, or socket, lined with a layer of relatively tough epithelial tissue 22. The tract is formed in the subcutaneous layer 23 overlying the skull 24.

Preferably, the surgical technique used in forming each of the tracts is as follows. Two, parallel transverse incisions each about 5.0 mm in length and about 1.5 cm apart, are made in the epidermis. The incisions coincide with and eventually form the linear openings 17 and 18. Subcutaneous tissue between the two incisions is then dissected away to afford sufficient space for two face to face strips of full thickness skin graft, 5 mm wide and slightly in excess of 1.5 cm in length. The top surfaces of the two strips of skin face each other so that when the strips are inserted in the dissected area and healing has taken place, a tract lined fully with the epithelial tissue 22 is provided.

After healing is completed, the hairpiece 26 can be installed.

The hairpiece 26 ordinarily includes a base 27 formed of fabric mesh, or the like to which the hair strands are secured.

The hairpiece base 27, in turn, is fastened to the anchors, generally designated by the reference numeral 29 by threads 31.

Each of the anchors is bilaterally symmetrical about a longitudinal axis 32 so that when an anchor is installed, the anchor axis 32 underlies the respective longitudinal axis 14 of the tract with the two axes lying in substantially the same vertical plane.

As appears most clearly in FIGS. 2–5 the anchor 29 includes a subdermal portion 34 comprising a spaced pair of wires 36 of tissue-compatible material extending from the base end 37 of the anchor through a downwardly bowed section 35 so as to fit snugly, although not tightly, in the comparably bowed socket 21, or tunnel.

At the tip end 38 of the subdermal portion 34, the two wires 36 converge and join; and adjacent the tip end 38 where the subdermal portion emerges from the tunnel 21, the wires are curved and angularly inclined relative to the bowed portion 35 so as to follow the underlying contours and snugly overlie the subjacent scalp surface. The support provided by the scalp to the overlying horizontal distal portion 39 resists any vertically upward dislodging force exerted on the opposite, or base, end 37 of the anchor, such as might result from wind, water or other forces acting on the hairpiece, with the top wall of the tunnel forming a fulcrum.

At the base end 37 of the anchor 29 the two spaced wires 36 are recurved upwardly and forwardly, diverging somewhat over a primary portion 41, or wing base portion, then spreading farther apart in a more widely diverging secondary portion 42, and finally assuming a laterally flared wing portion 43, oriented substantially at right angles to the anchor axis, or even slightly recurved beyond the perpendicular to the axis.

Figure 5:
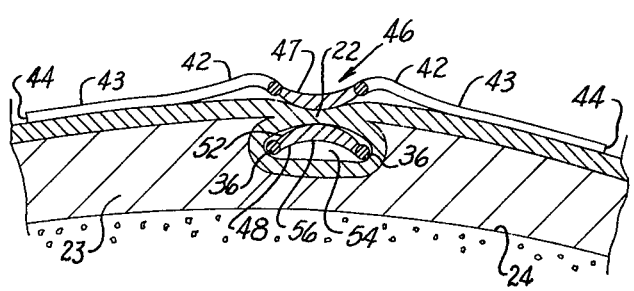
Figure 2:
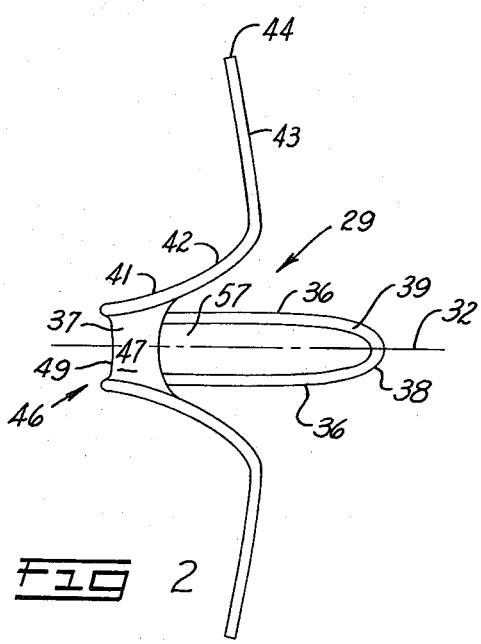
FIG. 2 is a top plan view, to a greatly enlarged scale, of a preferred embodiment of the hairpiece anchor of the invention.
Figure 3:
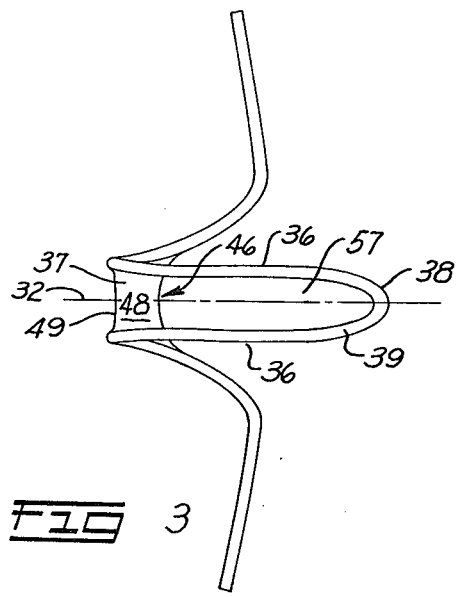
FIG. 3 is a bottom plan view of the embodiment shown in FIG. 2.

As will be particularly noted in FIG. 5, the second portion 42 and the third wing portion 43 assume an inverted dihedral such that the wings 43 follow the lateral slope of the scalp and the tips 44 of the wings lie almost in the horizontal plane of the subdermal portion 34 and thus cooperate with the subdermal portion in firmly confining the interposed longitudinal bridge 40 of tissue spanning the openings 17 and 18 (see FIGS. 1 and 4).

One of the most important features of the present embodiment is the web structure 46 located at the recurved base end 37 of the anchor.

The material of the web 46 is preferably tissue-compatible metal. However, a web of suitable "plastic" or fabric material can also be utilized.

As appears most clearly in FIGS. 2–5, the web 46 includes a top portion 47 spanning the primary wing portion 41 and a bottom portion 48 spanning the ends of the subdermal wires 36, for a distance approximately equal to the length of the top portion 47.

The top portion 47 and the bottom portion 48 of the web 46 are joined by an arcuate end portion 49 which follows the curvature of the base end 37 of the anchor.

When viewed in transverse section, as in FIG. 5, it will be noted that the top portion 47 of the web 46 is bowed arcuately downwardly with a resulting snug engagement between the lower surface of the top portion 47 and the underlying area of epithelial tissue 22 covering the longitudinal bridge 40 (see FIGS. 1 and 4) spanning the distance between the two linear openings 17 and 18.

The bottom portion 48 of the web 46, on the other hand, is arcuately bowed upwardly to a distance such that: (1) the upper surface 52 of the bottom portion 48 snugly engages the adjacent arcuate end portion 53 of the tract wall, and (2) a channel 54 is provided for the circulation of air through the tract tunnel 21.

In other words, the lower surface 56 of the bottom portion 48 of the web 46 forms an arch which ascends to a location above the bottoms of the wires 36. Air can therefore move to and fro in the arched area which, in turn, communicates with the passageway 57 defined by the two wires 36 as they traverse the length of the tract and emerge therefrom at the distal end where the wires are curved to conform to the underlying skin contour, as previously explained.

It is hygienically important that the tract be provided with air circulation; and the arched construction of the bottom portion 48 of the web not only fulfills this requirement, but also cooperates with the downwardly convex construction of the upper portion 47 of the web and the adjacent arcuate end portion 49 to confine the underlying skin tissue firmly yet comfortably.

Further, the substantially increased surface provided by the web is such that any dislodging forces are spread over a sufficient area of skin in contact with the web so that the hairpiece is comfortable to wear at all times.

The anchors 29 are so located on the hairpiece that when the hairpiece is to be installed and is properly oriented on the scalp, the anchors are superposed directly over the respective tracts. The anchors are then each manipulated so as to guide the tip end 38 through the opening 17 thence through the tunnel 21 until the tip 38 emerges from the opening 18. A slight additional forward movement is then given the anchor in the direction of the central location 16 on the scalp until the web 46 abuts and snugly engages the underlying skin tissue. The dimension of the anchor is such that at this juncture the distal end portion 39 of the anchor also firmly yet comfortably conforms with the underlying surface of the skin and the downwardly bowed portion 35 closely fits the shape of the tunnel.

This procedure is followed until all of the anchors are installed in their respective tracts. The scalp as well as the hairpiece afford the requisite amount of yield and resiliency so that installation is readily effected, yet when the installation is completed, a secure, comfortable fit is provided.

The close engagement of the distal portion 39 with the underlying scalp and the snug fit between the three portions 47, 48 and 49 of the web 46 and the bridge 40 of epithelial tissue firmly yet comfortably resist even vigorous buffetings suffered by the hairpiece and the arched channel formed by the web portion 48 with the communicating passageway 57 assures freedom of air movement to and fro in the tract tunnel 21.

What is claimed:

1. A hairpiece anchor comprising:
   a. an external portion including an upper pair of wires symmetrically disposed on opposite sides of an upper longitudinal axis and extending from an upper base end through a first flared section and a second more divergingly flared section terminating in a pair of laterally oriented tips substantially at right angles to said upper longitudinal axis;
   b. a subdermal portion engageable with a scalp tract having a tunnel with predetermined width and length, said subdermal portion of said anchor including a lower pair of wires symmetrically disposed on opposite sides of a lower longitudinal axis parallel to said upper axis and extending with a downward bow from a lower base end through said predetermined length, said pair of wires continuing further in a recurved linear extension converging to form a rounded tip,
   said linear extension having a length and contour such that said linear extension is capable of protruding exteriorly from the tunnel when said anchor is installed in a tract, and of engaging an underlying planar portion of the scalp adjacent the tunnel for a sufficient distance as to enable said anchor to resist a substantial upward force applied to said lower base end and tending to urge said linear extension in a downward direction by lever action with the top wall of the tunnel forming a fulcrum; and,
   c. an arcuate transition portion comprising a pair of wires joining said upper pair of wires and said lower pair of wires, said transition portion including an upper web spanning said upper base end, a lower web spanning said lower base end, and a transition web spanning said arcuate transition portion, the widths of said lower base end and said transition portion being substantially equal to said predetermined width of the tunnel, with said upper web, said transition web and said lower web being contoured to engage the interposed tract portion overlying the tunnel,
   said lower web being arched upwardly in lateral cross section to define a channel for the circulation of air.

2. A hairpiece anchor as in claim 1 in which said lower pair of wires extend in substantially parallel relation from said lower base end to said linear extension and in which said pair of wires defines a passageway in communication with said channel for the circulation of air throughout the entire length of said tunnel.

3. A hairpiece anchor as in claim 2 in which said upper web is bowed downwardly in lateral cross section for cooperation with said upwardly arched lower web in snugly engaging the interposed tract portion overlying the tunnel.

4. A hairpiece anchor as in claim 3 in which said flared sections of said upper pair of wires form an inverted dihedral.

* * * * *